United States Patent [19]

Bowman et al.

[11] Patent Number: 4,952,213
[45] Date of Patent: Aug. 28, 1990

[54] TIBIAL CUTTING GUIDE

[75] Inventors: Jerald A. Bowman; Larry G. McCleary, both of Warsaw, Ind.

[73] Assignee: Boehringer Mannheim Corporation, Indianapolis, Ind.

[21] Appl. No.: 306,523

[22] Filed: Feb. 3, 1989

[51] Int. Cl.⁵ .............................................. A61F 5/00
[52] U.S. Cl. ...................................... 606/79; 606/88; 606/62
[58] Field of Search .............. 128/92 R, 92 Z, 92 ZZ, 128/92 YZ, 92 V, 92 VY, 92 VV, 92 VW, 92 VD; 623/16, 17; 606/62, 53, 57, 96, 82, 88, 78, 79

[56] References Cited

U.S. PATENT DOCUMENTS

| | | | |
|---|---|---|---|
| 4,457,307 | 7/1984 | Stillwell | 128/92 VW |
| 4,467,801 | 8/1984 | Whiteside | 128/303 R |
| 4,474,177 | 10/1984 | Whiteside | 128/92 R |
| 4,524,766 | 6/1985 | Petersen | 128/92 VW |
| 4,574,794 | 3/1986 | Cook | 128/92 VW |
| 4,653,468 | 3/1987 | Kenna | 128/92 VW |
| 4,703,751 | 11/1987 | Pohl | 128/92 VW |
| 4,722,330 | 2/1988 | Russell | 128/92 VW |
| 4,736,737 | 4/1988 | Fargie | 128/92 VY |
| 4,738,253 | 4/1988 | Buechel | 128/92 VW |
| 4,759,350 | 7/1988 | Dunn | 128/92 VW |
| 4,787,383 | 11/1988 | Kenna | 128/303 R |

Primary Examiner—Robert A. Hafer
Assistant Examiner—Michael Brown
Attorney, Agent, or Firm—Barnes & Thornburg

[57] ABSTRACT

An apparatus for placing a bone cutting saw cutting guide adjacent a proximal surface of a human tibia bone having an elongated rod inserted into the tibia for clampingly supporting a rotating bar on the central longitudinal axis of the tibia bone. The bar being extended from the rod and connected to a pivot device which in turn is connected to a support arm that holds a saw cutting guide against a proximal portion of the tibia bone. The rotation angle of the rod determining the medial-lateral inclination of the saw cutting guide and the pivot device determining the anterior-posterior inclination of the saw cutting guide. The support arm is adjustable in length to determine the height of the saw cutting guide.

16 Claims, 2 Drawing Sheets

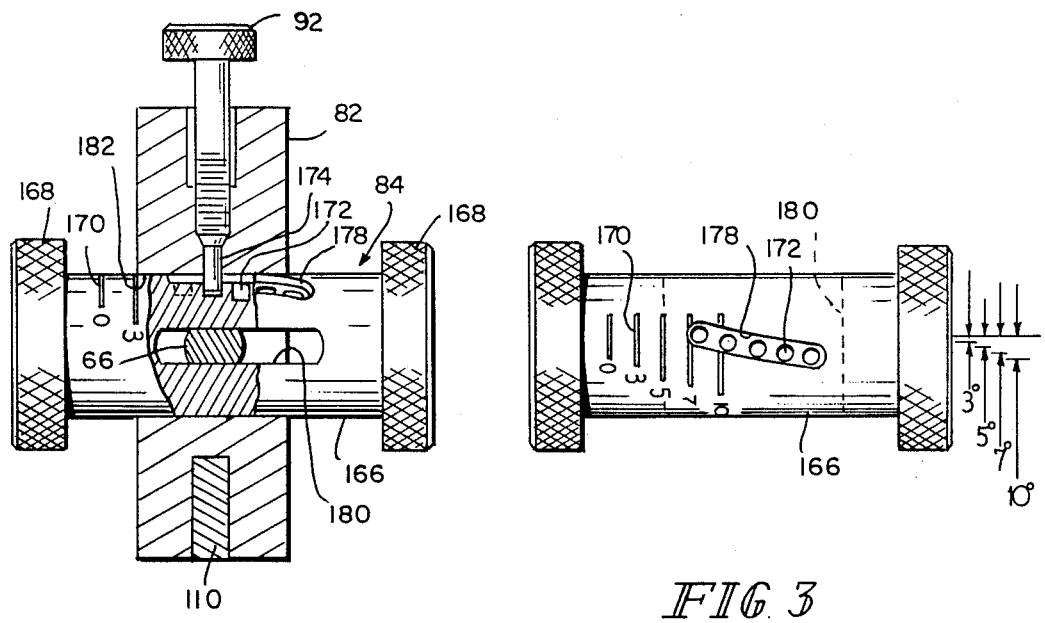
FIG. 2
FIG. 3
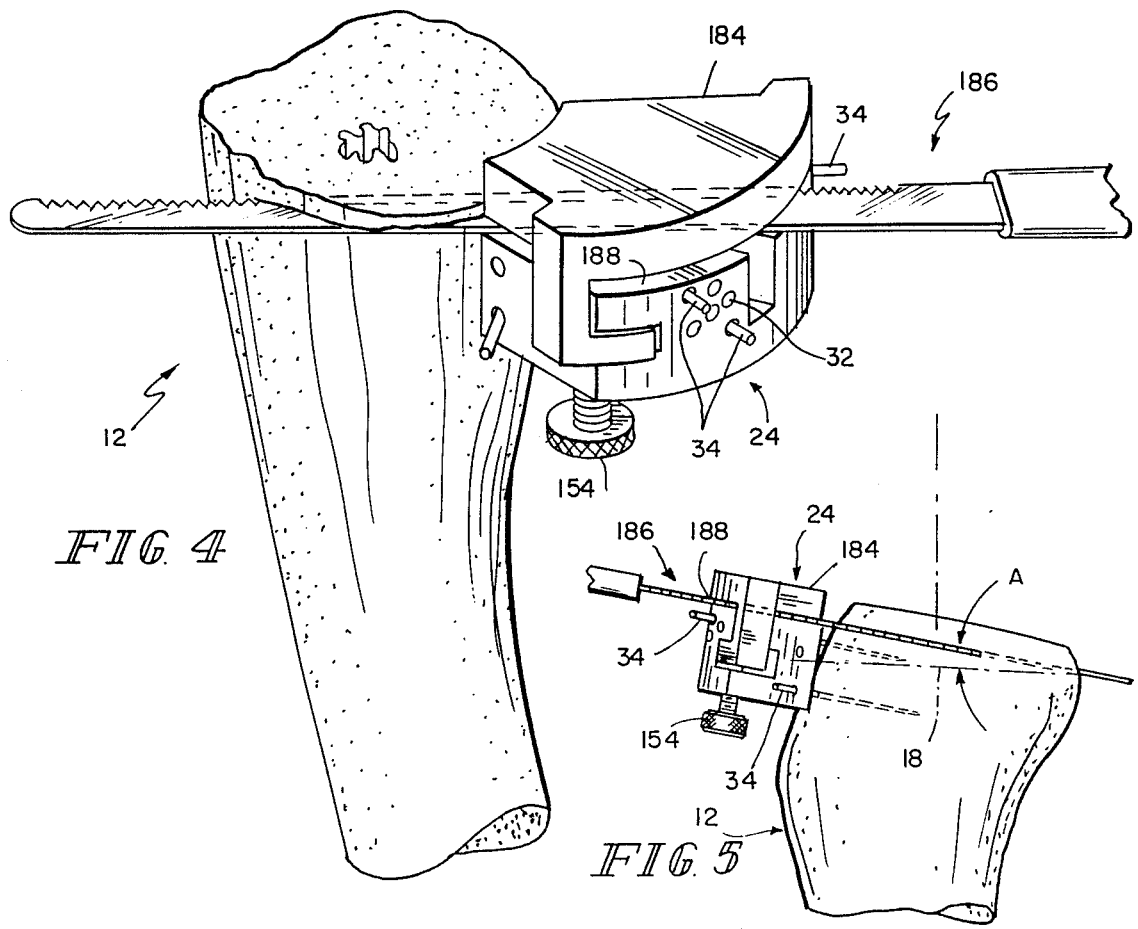
FIG. 4
FIG. 5

TIBIAL CUTTING GUIDE

BACKGROUND AND SUMMARY OF THE INVENTION

The present invention relates to a saw guide which permits a cut to be made in a material at a desired angular orientation. More particularly, the present invention relates to a saw guide for controlling the resection of an upper part of a human tibia bone to prepare the bone for placement of the tibial portion of a knee prosthesis. The present invention permits a cut or resection to be made at a desired angular orientation, with the angular orientation being adjustable to meet the needs of the patient.

As a part of the surgical procedure for the implant of a knee prosthesis, the upper or proximal portion of the human tibia bone must normally be resected. This resection is necessary both to remove the damaged portion of the tibial joint, and to prepare a surface for placement of the tibial portion of the knee prosthesis. As will be understood, it is of vital importance to prepare the surface of the tibia that is to receive the component as accurately as possible. Accurate orientation of the tibial surface is critical because, in such a surgical procedure, the surgeons performing the operation are attempting to duplicate as closely as possible the function of the normal human knee. Thus, proper alignment of the artificial prosthesis is necessary to permit the artificial knee to appear normal, and to function in a normal manner. Because the anatomy and configuration of individual knees differs considerably between individuals, it would be highly desirable to be able to select an orientation of the tibial surface at the time of the resection to closely duplicate the orientation and configuration of the opposite or contralateral side of the patient.

Conventional tibial resection guides are generally placed external to the tibia bone and generally provide for only one angular orientation of the cut and are bulky in size. Thus, it is generally not possible with conventional tibial resection guides to select the angle at which the tibial resection is performed without changing the tibial resection guide to a different guide with a different angular orientation. Thus, conventional tibial resection guides are limited in that, should the surgeon decide that a non-standard angular orientation is desirable to suit the needs of the particular patient, such an angular orientation may be impossible, or difficult to achieve because of the inability of the conventional tibial resection guide to be adjusted to provide such a desired angular orientation.

It is therefore one object of the present invention to provide a tibial cutting guide which permits adjustment and selection of the proper angular orientation of the tibial surface to be formed during the resection procedure.

Another object of the present invention is to provide a tibial cutting guide which can be adjusted to different angular orientations in more than one plane.

Yet another object of the present invention is to provide a tibial cutting guide in which the depth of the cut of the proximal portion of the tibia can be easily selected so that only the minimum amount of bone needs to be resected to prepare the tibial surface.

According to the present invention, an apparatus for preparing a proximal surface of a human tibia bone to receive a tibial portion of a knee prosthesis is provided. The tibia bone has an anterior-posterior axis, a medial-lateral axis, and a central longitudinal (or anatomic) axis. The apparatus includes means for establishing a first axis that is generally parallel to the central longitudinal (anatomic) axis of the tibia bone. The apparatus also includes means for guiding a cutting blade into cutting engagement with a proximal portion of the tibia bone. Means for selectively adjusting the position of the guiding means along a first axis is provided as well as means for angularly orienting the guiding means with respect to a first plane that is perpendicular to the first axis. This allows the guiding means to be properly positioned adjacent the proximal portion of the tibia bone to permit a portion of the bone to be resected to receive the tibia portion of the knee prosthesis.

One feature of the foregoing structure is that means are provided for selectively adjusting the position of the guiding means along the first axis. One advantage of this feature is that, by permitting adjustment of the guiding means along the first axis, the depth of the cut to be made in the proximal portion of the bone can be adjusted so that the minimum amount of bone can be resected.

Another feature of the foregoing structure is that means for angularly orienting the guiding means with respect to a first plane that is perpendicular to the first axis is provided. By permitting selective angular orientation of the guiding means with respect to the first plane, the angular orientation of the cut to be made in the knee, and consequently the angular orientation of the resected tibial surface can be adjusted and selected according to the anatomical requirements of the individual patient at the time of the resection.

In preferred embodiments of the present invention, the adjusting means includes a first height adjusting device that is mounted on the end of an elongated rod that is adapted to be inserted into the medullary canal in the tibia bone. One feature of the foregoing structure is that, by utilizing an elongated rod that fits into the medullary canal within the tibia bone, stabilization and alignment of the apparatus is provided with reference to the tibia bone itself. One advantage of this feature is that more accurate stabilization and alignment of the device is provided.

Also in preferred embodiments of the present invention, the orienting means includes a pivot device that is cantilevered away from the first height adjusting device and that is attached to the guiding means to permit limited pivotal movement around a second axis that is generally parallel to the medial-lateral axis of the tibia bone. This limited pivotal movement about the second axis permits adjustment of the angular orientation of the guiding means relative to a third axis that is generally parallel to the anterior-posterior axis of the bone. One feature of the foregoing structure is that a pivot device is provided that is capable of rotation about an axis to permit selective adjustment of the angular orientation of the guiding means. One advantage of this feature is that the angular orientation of the guiding means, and consequently the angular orientation of the cut that is to be made in the tibia bone can be selectively adjusted to meet the requirements of the individual patient at the time the cut is to be made and/or to accommodate different surgical techniques, i.e. revision, total knee replacement, osteotomies, etc.

Thus, the present invention provides a tibial cutting guide which permits the angular orientation of the cut to be adjusted to meet the requirements of the patient. The angular orientation of the cutting guide, and consequently the angular orientation of the tibial surface after the bone has been resected, can be changed along two planes, which greatly increases the different angular combinations available to the surgeon. These angular combinations can be chosen by the surgeon while the invention is in place on the patient. Thus, it is not necessary to select differently oriented cutting guides to change the angular orientation of the cut.

Additional objects, features, and advantages of the present invention will be apparent to those skilled in the art upon consideration of the following detailed description of a preferred embodiment exemplifying the best mode of carrying out the invention as presently perceived.

BRIEF DESCRIPTION OF THE DRAWINGS

FIG. 2 is a sectional view of the pivot block exposing the locking cylinder with portions broken away;

FIG. 3 is a top plan view of the locking cylinder;

FIG. 4 is a view similar to FIG. 1 with the cutting guide properly positioned and attached to the tibia;

FIG. 5 is an elevational view of the cutting guide and saw illustrating a selected angular orientation of the cut in the tibia.

DETAILED DESCRIPTION OF THE DRAWINGS

Figure 1:
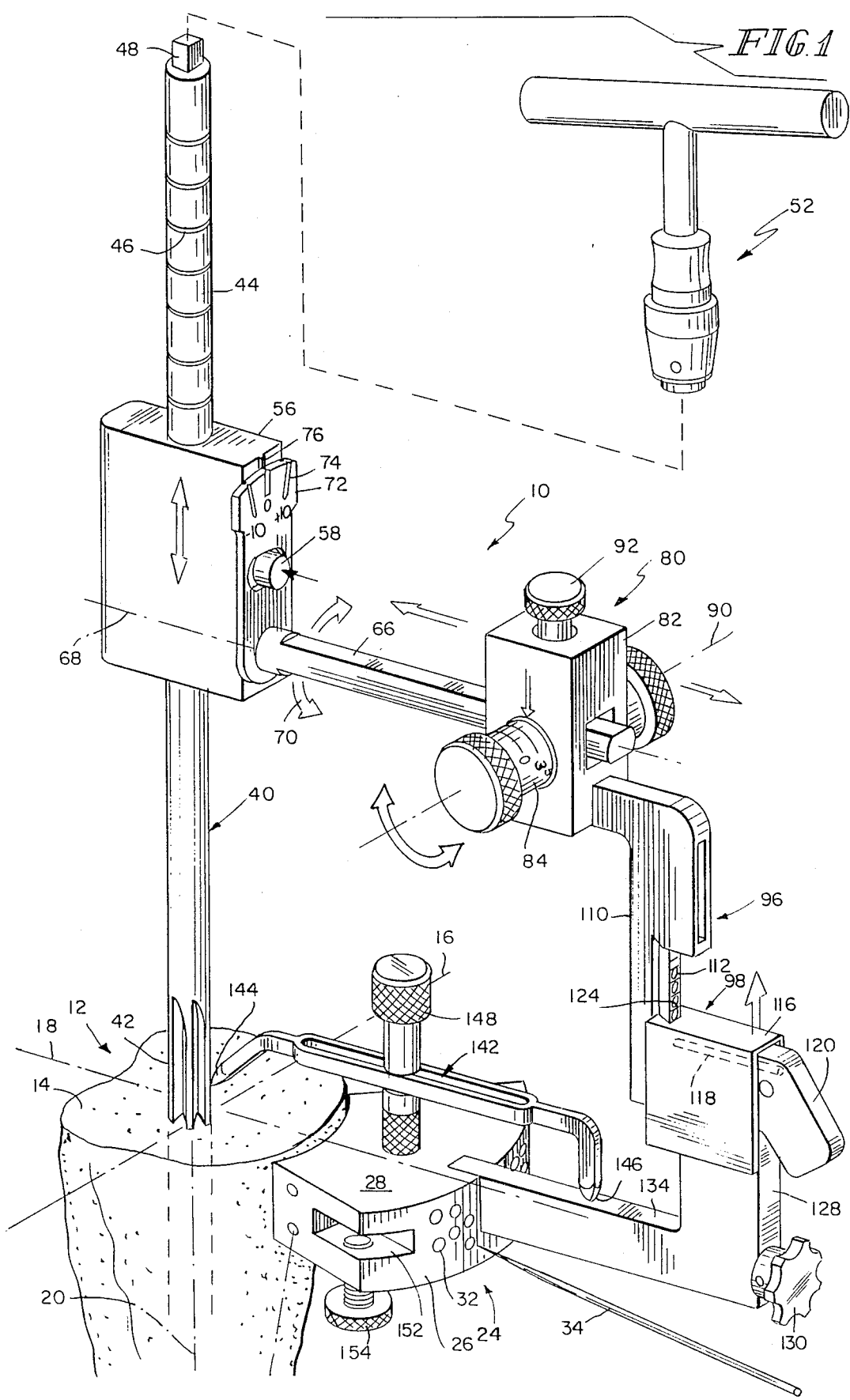
FIG. 1 is a perspective view of the tibial cutting guide according to the present invention in an operative position on a human tibia bone.

Referring now to the drawings, FIG. 1 illustrates the tibial cutting apparatus 10 according to the present invention in a representative position on the proximal portion of a tibia bone 12. It will be understood that the tibial bone is being prepared for a resection procedure in which a portion of the tibia bone 12 will be removed to create a tibial surface for placement of the tibial portion of a knee prosthesis (not shown). It will be further understood that the preparation of the resected tibial surface is of utmost importance in the overall outcome of the placement of the prosthesis. Thus, the cut that is made to resect the upper portion of the tibia bone 12 must be accurately placed and oriented to create a tibial surface that is in the proper angular orientation to receive the tibial portion of the prosthesis.

The tibia bone 12 includes a proximal surface 14 which, although not shown in great detail, represents the natural proximal surface of the bone 12. It is this upper surface which is to be resected in the surgical procedure. For reference purposes, it is understood by those skilled in this area that the tibia bone can define various axes. Specifically, a cross-wise axis extending from one side of the tibia bone 12 to the other side of the tibia bone 12 is referred to as the medial-lateral axis and is identified as the axis 16 in FIG. 1. Likewise, a front-to-back axis is defined as the anterior-posterior axis and is identified by the axis line 18. These two axis, as well as a generally vertical axis extending generally lengthwise through the tibia bone 12 and generally corresponding to an axis defined by the medullary canal will be referred to as the longitudinal or anatomic axis and is identified by the axis line 20.

To provide for accurate placement and control of the cut to be made in the bone 12, a saw guide assembly 24 is provided that is shown placed adjacent an anterior portion of the bone 12. It is the placement of this saw guide assembly 24 that controls the cut to be made in the bone 12. Thus, the remaining portion of the apparatus 10 is used to provide for highly accurate placement of the saw guide assembly 24 in relation to the bone 12. As it will be described below, after the saw guide assembly 24 has been accurately placed using the entire apparatus 10, the major portion of the apparatus 10 except for the saw guide assembly 24 is removed away from the bone 12 with the guide assembly 24 left attached to the bone 12 to guide a saw (not shown) to control the cut to be made in the bone 12.

The guide assembly 24 includes a cutting block 26 that has an upper cutting surface 28 on which the saw (not shown) will rest and be guided. The cutting block 26 includes a plurality of pin bores 32 through which locating and retaining pins 34 are placed after the guide assembly 24 has been accurately positioned with respect to the bone 12. The pins 34 are actually inserted into the bone 12 to retain the guide assembly 24 in its previously placed position.

An intermedullary rod 40 is illustrated that is adapted to be placed into the medullary canal (not shown) in the bone 12. The rod 40 includes a first end 42 that is adapted to be inserted into the canal, and in the illustrative embodiment includes some type of flutes or threads to aid in this insertion. The rod 40 includes a second opposite end 44 which is formed to include a plurality of spaced-apart, circumferentially extending grooves 46. The use of the grooves 46 will be described below in connection with the positioning of a portion of the apparatus 10. A drive end 48 is provided on the extreme proximal end of the rod 40, with the drive end 48 adapted to receive a drive handle 52 which is used to actually insert the rod 40 into the canal within the bone 12. After the insertion is complete, the drive handle 52 is detached to prevent interference with the remainder of the procedure.

A slideable locking device 56 is provided that is disposed over, and is slideably movable on, the rod 40. The locking device 56 includes a plunger mechanism 58 which (although not shown in detail) permits the locking device 56 to engage one of the spaced-apart grooves 46 to selectively position the locking device on the rod 40 at different locations. The details of the plunger 58, and its use to engage one of the grooves 46 to selectively position the locking device 56 is structurally similar to the plunger mechanism illustrated and described in U.S. Pat. No. 4,710,075 which is assigned to the assignee of the present invention. The entire disclosure of U.S. Pat. No. 4,710,075 is herewith incorporated by reference to describe the structure and use of the plunger 58.

A support bar 66 is cantilevered from the locking device 56 and extends along a third axis that is generally parallel to the anterior-posterior axis 18 and is identified by the axis line 68. The support bar 66 is journaled for rotational movement in the locking device 56 and is rotatable in either direction as indicated by the double arrows 70. A flexible plate 72 is rigidly attached to the end of the support bar 66 adjacent the locking device 56, with the flexible plate 72 acting both to define the rotational movement of the support bar 66 and to provide an indication of the amount of angular movement of the support bar 66.

The plate 72 includes a channel through which the plunger 58 extends, with the channel and the plunger 58 cooperating to limit the rotational movement of the bar 66. Indices 74 are provided at the top of the flexible plate 72 to provide an indication of the angular movement of the bar 66. AdditionallY, a protruding rib 76 extends from the locking device 56 and cooperates with grooves (not shown) formed in the back of the flexible plate 72 to releasably lock the flexible plate 72 in one of the three angular positions. Thus, the grooves act as detents into which the rib 76 extends, with the flexibility of the plate 72 utilized to prevent movement of the bar 66 and plate 72 unless a certain excess force is applied thereby overcoming the flexible pressure applied by the plate 72. For illustrative purposes, the angular movement of the bar 66 is limited from +10° to −10°, and the three indices 74 are set at −10°, 0°, 0°, and +10°, but these angles are arbitrary and set by the flexible plate 72 extremes.

The angular movement of the support bar 66 about the third axis 68 acts to impart angular changes to the saw guide assembly 24 with respect to the medial-lateral axis 16. Thus, the rotational movement of the support bar 66 as indicated by the indices 74 acts to control the angular orientation of the resulting cut on the proximal surface of the bone 12 with respect to the medial-lateral axis 16. It will be understood by those skilled in the art that this particular angular orientation of the cut, and of the resulting tibial platform with respect to the medial-lateral axis 16, controls the varus/valgus positioning of the overall leg alignment of the installed prosthesis. This varus/valgus positioning can thus be controlled and dictated by the selection of the angular orientation of the saw guide assembly 24 with respect to the medial-lateral axis 16 by utilizing the rotational characteristics of the support bar 66 within the locking device 56. An external alignment device (not shown) may be used to make this varus/valgus adjustment as will be understood by these skilled in the art.

A pivot device 80 is provided at the distal end of the support bar 66 to provide for limited rotational movement about an axis 90 which is generally parallel to the medial-lateral axis 16. It will be understood that this rotational movement of the pivot device 80 about the axis 90 permits changes in the angular orientation of the saw guide assembly 24 with respect to the anterior-posterior axis 18. As will be further understood, changes in the angular orientation of the saw guide assembly 24 with respect to the anterior-posterior axis 18, and consequentlY of the cut formed in the bone 12, controls the anterior-posterior slope of the resected tibial surface that will receive the tibial component of the prosthesis. The present invention thus permits selection of the anterior-posterior slope as desired. Normally, the range of the anterior-posterior slope is from 0°, or level, to 12° posterior slope. On the average, a 7° posterior slope would be considered a typical slope. As will be described below, the present invention permits selection of varying posterior slopes from 0° to 10° posterior, with the specific settings being 0°, 3° posterior, 5° posterior, 7° posterior, and 10° posterior, but these angles are arbitrary and defined by the device extremes.

A locking cylinder 84 is provided within the pivot block 82 which permits the selection of the desired angular orientation between 0° and 10°. A spring locking pin 92 is provided in the top of the pivot block 82 which cooperates with the locking cylinder 84 to lock the pivot block in one of the selected angular orientations, i.e. 0°, 3°, 5°, etc. The details of this mechanism will be described below in the discussion related to FIGS. 2 and 3.

A support arm assembly 96 depends from the pivot device 80 to support the saw guide assembly 24. The support arm assembly 96 includes a height adjusting assembly 98 for changing the relative height or position of the saw guide assembly 24 with respect to the pivot device 80. As will be described below, the height adjusting assembly 98 is utilized to control the depth of the cut that will be placed in tibia bone 12.

The support arm 96 includes an upper vertical support arm 110 which is directly attached to the pivot block 82, and a lower support arm 128. Vertically aligned locking holes 112 are provided in the upper vertical support arm 110 which cooperate with a latching mechanism 116 on the lower support arm 128 to provide the height adjustment features of the height adjusting assembly 98. Specifically, a locking pin 118 is provided that is configured to engage one of the spaced-apart locking holes 112. The locking pine 118 is released from the designated hole 112 by actuation of the trigger 120. Thus, to adjust the height of the lower support arm 128 with respect to the upper vertical support arm 110, and consequently the height of the saw guide assembly 24, the trigger 120 is depressed which withdraws the locking pin 118 from one of the holes 112. The locking assembly 116 and attached lower support arm 128 are then moved either upwardly or downwardly until the correct height position is achieved. The trigger 120 is then released which permits the pin 118 to engage the desired locking hole 112. To provide for accurate height adjustment, indices 124 may be provided adjacent the vertically aligned locking holes 112 to provide for an indication of the actual height adjustment being obtained by movement of the latching mechanism 116. Illustratively, the locking holes 112, and the indices 124, are spaced 2 millimeters apart to provide for 2 millimeter height adjustment increments of the latching mechanism 116 and consequently of the saw guide assembly 24, but these increments are arbitrary.

A screw (not shown) and attached screw knob 130 are provided in the lower support arm 128 to attach the saw guide assembly 24 to that lower support arm 128. As will be understood, the screw is embedded in the lower support arm 128 and is configured to engage the rear portion of the saw guide assembly 24 so that the saw guide assembly 24 can be easily detached from the lower support arm 128 and the remainder of the apparatus 10 after the saw guide 24 has been properly positioned adjacent the tibia bone 10. The lower support arm 128 includes an upper arm surface 134 that is generally planar and that is configured to be in alignment with the cutting surface 28 of the saw guide assembly 24 when the assembly 24 is attached to the lower support arm 128.

A stylus 142 is provided that includes a first end 144 and a second end 146. The stylus is attached to the upper portion of the saw guide assembly 24 by a removable attaching screw 148. The purpose of the stylus 142 is to aid in positioning the saw guide assembly 24 relative the bone 12 so that a proper depth of cut or resection can be determined and set using the height adjusting assembly 98. It will be understood that the configuration of the stylus 142 is not critical so long as the first end 144 is at the same level as the cutting surface 28 so that the positioning of the first end 144 at a desired reference level corresponds to placement of the cutting surface 28 at that same reference level.

In the illustrated embodiment, the second end 146 of the stylus 142 is configured to be placed in contact with the upper arm surface 134 of the lower support arm 128. The first end 144 of the stylus 142 is configured to be placed on the lowest portion of the uncut proximal surface of the bone 12. With the first end 144 of the stylus 142 positioned on the lowest surface of the proximal portion of the bone 12, the cutting surface 28 will thus be aligned with the lowest portion of the surface of the bone 12. This alignment of the cutting surface 28 with the lowest portion of the surface of the bone 12 is assured because of the relationship between the upper arm surface 134 and the cutting surface 28. Because the second end 146 of the stylus 142 is placed on the upper arm surface 134, the second end 146 of the stylus 142 is thus aligned and at the same level as the cutting surface.

Thus, when the first end 144 of the stylus 142 is positioned on the lowest portion of the tibia bone 12, the cutting surface 28 is also aligned with that same lowest portion. It will be understood that, although it is normally desirable to align the cutting surface 28 with the lowest portion of the tibia bone 12 so that the cut to be made prepares a flat planar surface, there may be instances where the lowest portion of the bone 12 is not utilized as a reference. This would be true where, for whatever reason, there was an abnormally low spot in the upper surface of the tibia bone 12. Such an abnormally low spot would require the removal of an excess amount of bone if the cut were made in reference to that low spot. However, under normal circumstances, the alignment of the cutting surface 28, and thus the alignment of the cut that is to be made will be made in reference to the low spot on the upper surface of the bone 12.

The saw guide assembly 24 is also formed to include two receiving slots 152 (only one of which is shown in FIG. 1) for receiving an upper guide plate (or saw capture plate) (shown in FIG. 4) which can be attached to the saw guide assembly 24 before or after the guide assembly 24 has been properly positioned relative to the bone 12. Locking screws 154 are provided to secure the guide plate 184 to the guide assembly 24 after the saw guide assembly 24 is separated from the remainder of the apparatus 10. The use of the guide plate 184 will be discussed below in the discussion related to FIG. 4.

In operation, the rod 40 is first inserted into the medullary canal in the bone 12 to provide an axis of alignment and to stabilize the apparatus 10. After the rod 40 has been inserted, the locking device 56 is positioned over the rod 40 and locked at the desired position in one of the grooves 46. The selection of the position of the locking device 56 will be dictated the position of the first end 144 of the stylus 142 relative to the lowest point on the proximal surface of the tibial bone 12. The height adjusting assembly 98 will normally be in the fully elevated position during this preliminary installation step. After the locking device 56 has been properly positioned utilizing the position of the stylus 142, the angular orientation of the saw guide assembly 24 is then adjusted to meet the needs of the patient, and also to meet the requirement of the prosthesis that is to be installed within the patient. As discussed above, the support bar 66 can be rotated to +10°, −10°, or any orientation in between, to adjust the varus-valgus alignment of the tibial surface that is to be formed during the resection. Again, this adjustment changes the angular orientation of the saw guide assembly 24 relative to the medial-lateral axis 16. After this adjustment has been made, the pivot device 80 is utilized to adjust the angular orientation of the saw guide assembly 24 relative to the anterior-posterior axis 18. In the preferred embodiment, the possible angular orientations are 0°, and 3°, 5°, 7°, or 10° posterior slope.

To make this angular adjustment relative to the anterior-posterior axis 18, the spring-locking pin 92 is pulled up from the pivot block 82 which then permits the pivot block 82 to be rotated about the locking cylinder 84. The locking cylinder 84 is slidable laterally along the axis 90 to position locking holes (illustrated in FIGS. 2 and 3) with the end of the spring locking pin 92. The actual interior structure of the pivot block 82 and the locking cylinder 84 will be discussed below in the discussion related to FIGS. 2 and 3. After the correct angular orientation is set, the spring locking pin is lowered to lock the pivot block 82 and attach support arm assembly 96 in this desired angular orientation.

After all of the desired angular changes and settings have been made, a final check is normally made to ensure that the first end 144 of the stylus 142 is still in contact with the desired reference position which is normally the lowest portion of the tibia bone 12. If, for some reason, the stylus 142 is not in contact with the desired reference position, small height adjustments can be made utilizing the height adjusting assembly 98. After the stylus has been checked for proper position, the stylus 142 is removed from the saw guide assembly 24 by removal of the attaching screw 148. At this point, the surgeon determines the desired depth of the cut that is to be made into the bone 12. Normally, it is desirable to remove the minimum amount of bone that will still provide a suitable tibial resected surface. The depth of cut can then be adjusted by lowering the height adjusting assembly 98 to the desired cut depth. As discussed above, this cut depth can be adjusted in two millimeter increments by lowering the height adjusting assembly 98 and utilizing the indices 124.

After this height adjustment has been made, the saw guide assembly 24 is now in the proper position for the cut, and is then rigidly attached to the tibia bone 12. This attachment is made by utilizing the pins 34 which are inserted through the holes 32 in the saw guide assembly 24. After the saw guide assembly 24 has been rigidly attached to the tibia bone 12, the remainder of the apparatus 10 is removed by unscrewing the screw knob 130 to detach the support arm 128 from the saw guide assembly 24. Thus, at this point in the procedure, the saw guide assembly 24 is properly positioned adjacent the tibia bone 12 in a proper angular orientation and at the proper depth to make the desired resection of the bone 12 to produce the proper tibial surface for receipt of the tibial component of the knee prosthesis.

FIG. 2 shows in greater detail the structure of the pivot block 82 and the cooperating locking cylinder 84 which permits the angular adjustment of the pivot device 80. The locking cylinder 84 includes a barrel portion 166 and two end knobs 168. Indices 170 are provided on the surface of the barrel 166 to provide an indication to the surgeon of the angular orientation of the pivot device 80. Locking holes 172 are provided in the barrel 166 which are sized and configured to receive a locking end 174 of the spring locking pin 92. The locking holes 172 are positioned in a channel 178 which aids in locating the locking end 174 of the pin 92 over the desired hole 172. A slot 180 is formed through the center of the barrel 166, with the slot 180 being sized to fit over the support arm 166 such that no rotational movement of the locking cylinder 84 will be permitted. The pivot block 82 is formed to include an opening 182 that is sized to receive the barrel 166 of the locking cylinder 84 such rotation of the pivot block 82 around the locking cylinder 84 is permitted. Thus, with the spring locking pin 92 disengaged from one of the locking holes 172, the pivot block 82 is pivotal around the stationary locking cylinder.

As can be seen in FIG. 3, the locking holes 172 are angularly offset along the circumference of the barrel 166. Additionally, the locking holes 172 are axially spaced along the barrel 166. As the pivot block 82 is rotated to one of the desired angular orientations, i.e. between 0° and 10°, the locking cylinder 84 can be moved laterally within the pivot block 82 until the desired locking hole 172 aligns with the locking end 174 of the spring locking pin 92. The channel 178 around the locking holes 172 acts to prevent dislocation of the locking end 174 from the vicinity of the locking holes 172. The indices 170 are provided which provide an indication to the operator of the angular orientation between the pivot block 82 and the locking cylinder 84. The indices 170 actually provide an indication of a lateral position of the locking cylinder 84, however, because of the lateral and radial alignment of the locking holes 172, the indices 170 also provide an indication of the angular orientation in which the pivot block 82 has been locked relative to the locking cylinder 84.

FIG. 4 illustrates the positioning of the saw guide assembly 24 after the remainder of the apparatus 10 has been removed, and with the guide plate 184 installed in place. As can be seen, with the guide plate 184 installed on the saw guide assembly 24, a slot 188 is formed through which a saw blade 186 is inserted. This slot 188 acts to guide the saw 186 such that an accurate cutting or resection of the tibia bone 12 is performed. As discussed above, with the saw guide assembly 24 rigidly attached to the bone in the proper angular orientation, the resulting cut made by the saw 186 will form a tibial surface having a desired angular orientation that meets the requirements of the patient and of the prosthesis to be implanted.

FIG. 5 illustrates in somewhat greater detail the positioning of the saw guide assembly 24 over the anterior portion of the tibia bone 12. In this illustrative example, the angle selected is illustrated by the angle A which, for example, may be 10° posterior slope relative to the anterior-posterior axis 18. However, as discussed above, this posterior slope can be adjusted anywhere from 0° to 10° slope which permits the surgeon to select the appropriate slope depending upon the individual requirements.

As can be seen, the present invention provides an apparatus for accurately and properly positioning a saw guide such that the resection of the proximal portion of a tibia bone can be performed accurately, with the resulting resected tibial surface having the correct angular orientation as dictated by the needs of the patient and by the requirements of the prosthesis to be implanted. The invention utilizes a stabilizing rod which both stabilizes the devices and acts as a reference axis from which the angular orientation of the saw guide may be adjusted. Once the saw guide has been properly positioned in a desired angular orientation, and the depth of the cut to be made in the bone has been set, this saw guide can be rigidly attached to the bone, with the remainder of the apparatus removed. The ability to select the desired angular orientation and depth of cut utilizing a common positioning apparatus provides the advantage to the surgeon of being able to make last minute changes in the parameters of the resection without the necessity of removing the positioning device and utilizing a differently orientated device.

Although the invention has been described in detail with reference to a preferred embodiment in specific examples, variations and modifications exist within the scope and spirit of the invention as described and defined in the following claims.

What is claimed:

1. An apparatus for preparing a proximal surface of a human tibia bone to receive a tibial portion of a knee prosthesis, the tibia bone having an anterior-posterior axis, a medial-lateral axis, and a central longitudinal axis, the apparatus comprising, means for establishing a first axis generally parallel to the central longitudinal axis of the tibia bone, means for guiding a cutting blade into cutting engagement with a proximal portion of the tibia bone, means for selectively adjusting the position of the guiding means along the first axis, and means for angularly adjusting the guiding means with respect to both the anterior-posterior axis and the medial-lateral axis to orient the guide means into a first plane defined by the anterior-posterior axis and the medial-lateral axis, such that the guiding means is properly positioned adjacent the proximal portion of the tibia bone to permit a portion of the proximal portion of the tibia bone to be resected to receive the tibial portion of a knee prosthesis.

2. The apparatus of claim 1, wherein the establishing means comprises an elongated rod that is formed to include a first end that is adapted to be inserted into a medullary canal in the tibia bone and a second end that extends upwardly out of the tibia bone when the first end is inserted into the bone.

3. An apparatus for preparing a proximal surface of a human tibia bone to receive a tibial portion of a knee prosthesis, the tibia bone having an anterior-posterior axis, a medial-lateral axis, and a central longitudinal axis, the apparatus comprising, means for establishing a first axis generally parallel to the central longitudinal axis of the tibia bone, means for guiding a cutting blade into cutting engagement with a proximal portion of the tibia bone, means for selectively adjusting the position of the guiding means along the first axis, and means for angularly orienting the guiding means with respect to a first plane defined by the anterior-posterior axis and the medial-lateral axis, such that the guiding means is properly positioned adjacent the proximal portion of the tibia bone to permit a portion of the proximal portion of the tibia bone to be resected to receive the tibial portion of a knee prosthesis, wherein the establishing means comprises an elongated rod that is formed to include a first end that is adapted to be inserted into a medullary canal in the tibia bone and a second end that extends upwardly out of the tibia bone when the first end is inserted into the bone, wherein the adjusting means comprises a first height adjusting device that is mounted on the second end of the elongated rod to permit height adjustment of the guiding means along the first axis and a second height adjusting device that is attached to the first adjustment device and which permits height adjustment of the guiding means relative to the first adjusting device along the first axis.

4. The apparatus of claim 3, wherein the orienting means comprises a pivot device that is cantilevered away from the first height adjusting device and that is attached to the guiding means to permit limited pivotal movement around a second axis generally parallel to the medial-lateral axis of the bone to adjust the angular orientation of the guiding means relative to the anterior-posterior axis of the bone.

5. The apparatus of claim 4, wherein the orienting means further comprises a support bar with a first end journaled for rotational movement within the first height adjusting device and a second opposite end adapted to support the pivot device, whereby the support bar can be rotated about a third axis generally parallel to the anterior-posterior axis to adjust the angular orientation of the guiding means relative to the medial-lateral axis.

6. An apparatus for orienting and controlling a cut to be made in a proximal portion of a human tibia bone to permit the bone to receive a tibial component of a knee prosthesis, the tibia bone having an anterior-posterior axis, a medial-lateral axis, and a central longitudinal axis, the apparatus comprisisng, an intermedullary rod adopted to be partially inserted into the tibia bone to define a first axis generally coincident with the central longitudinal axis, a locking device that is movable along the first axis and is releasably lockable at selected locations along the uninserted portion of the intermedullary rod, a saw guide for accurately controlling the placement of a cutting saw blade relative to the proximal portion of the tibia bone, and means connecting the saw guide to the locking device for angularly orienting the saw guide relative to the locking device to properly position the saw guide in a selected angular orientation adjacent the proximal portion of the bone to permit the bone to be resected to produce a proximal surface of the bone that has a desired angular orientation for receiving the tibial portion of the knee prosthesis.

7. The apparatus of claim 6, wherein the orienting means comprises a pivot device cantilevered from the locking device that is pivotable about a second axis generally parallel to the medial-lateral axis of the bone to adjust the angular orientation of the saw guide.

8. The apparatus of claim 7, wherein the orienting means further comprises a support bar having a first end journaled for rotational movement in the locking device for rotation about a third axis generally parallel to the anterior-posterior axis of the bone to permit selected angular adjustment of the saw guide relative to the second axis, with a second end supporting the pivot device.

9. The apparatus of claim 8, further comprising a height adjusting device separate from the locking device that is attached to the pivot device and the saw guide to permit height changes in the saw guide generally along its first axis.

10. The apparatus of claim 7, wherein the pivot device includes an angular locking pin and a pivot block with the pin attached to the support bar and extending through the pivot block to permit the pivot block to be rotated to selected lockable angular orientations with respect to the locking pin.

11. The apparatus of claim 6, further comprising a removable handle that is adapted to engage the proximal end of the intermedullary rod to permit the rod to be inserted into the tibia bone by an operator.

12. The apparatus of claim 11, further comprising means for releasably attaching the saw guide to the orienting means so that the saw guide can be separated from the orienting means after the saw guide has been properly positioned relative to the tibia bone.

13. An apparatus for positioning and controlling a cut to be made in a proximal portion of a human tibia bone to create a generally flat surface oriented in a desired angular orientation to receive a tibial component of a knee prosthesis, the apparatus comprising, a saw guide that is positionable adjacent an anterior portion of the proximal portion of the bone, the saw guide having a flat planar surface for guiding a saw blade to permit the saw blade to resect a selected amount of the proximal portion of the bone to create the generally flat surface oriented at the desired angular orientation, an intermedullary rod having a first end that is adapted to be inserted into a medullary canal within the bone, with the inserted rod defining a first axis, the rod having a second end that extends away from the proximal portion of the bone along the first axis when the first end is inserted into the bone, a locking device that is movable and selectively lockable at selected positions along the second end of the rod along the first axis, a support bar cantilevered away from the locking device along a third axis that is parallel to an anterior-posterior axis of the tibia bone, a pivot device mounted on the support bar that is pivotable and selectively positionable about a second axis that is parallel to a medial-lateral axis of the tibia bone, and means for connecting the saw guide to the pivot device so that the saw guide is angularly positionable about the second axis to control the angular orientation of the reserted surface of the bone with respect to the anterior-posterior axis of the bone and is positionable along the first axis to control the amount of the bone that is resected.

14. The apparatus of claim 13, wherein the connecting means includes a height adjustment device for adjusting the position of the saw guide along the first axis relative to the pivot device.

15. The apparatus of claim 13, wherein the support bar is journaled within the locking device such that rotational movement of the support bar is permitted about the third axis to adjust the angular orientation of the saw guide with respect to the second axis.

16. The apparatus of claim 13, wherein the pivot device includes a pivot block and a cylindral locking device, the cylindrical locking device being attached to the support bar such that rotation about the second axis is prevented, the pivot block mounted on the cylindrical locking device such that the pivot block is selectively rotatable about the cylindrical locking device to different lockable angular orientations.

* * * * *